United States Patent
Bartek et al.

(10) Patent No.: US 7,002,034 B2
(45) Date of Patent: Feb. 21, 2006

(54) METHOD FOR THE PRODUCTION OF BIPHENYL-4-CARBONITRILE

(76) Inventors: Johannes Bartek, Bäretstrasse 6a, CH-3930 Visp (CH); Pascal Willa, Niedergampelstrasse, CH-3945 Gampel (CH)

( * ) Notice: Subject to any disclaimer, the term of this patent is extended or adjusted under 35 U.S.C. 154(b) by 42 days.

(21) Appl. No.: 10/493,979

(22) PCT Filed: Oct. 28, 2002

(86) PCT No.: PCT/EP02/12008

§ 371 (c)(1),
(2), (4) Date: Apr. 29, 2004

(87) PCT Pub. No.: WO03/037848

PCT Pub. Date: May 8, 2003

(65) Prior Publication Data

US 2005/0085657 A1    Apr. 21, 2005

(30) Foreign Application Priority Data

Oct. 30, 2001 (EP) .................................. 01125852

(51) Int. Cl.
*C07C 253/04* (2006.01)

(52) U.S. Cl. .................................................. 558/332
(58) Field of Classification Search ................. 558/332
See application file for complete search history.

(56) References Cited

FOREIGN PATENT DOCUMENTS

| DE | 2737210 | 2/1979 |
|---|---|---|
| DE | 19833409 | 12/1998 |
| WO | 9616023 | 5/1996 |

*Primary Examiner*—Kamal A. Saeed
(74) *Attorney, Agent, or Firm*—Fisher Christen & Sabol

(57) ABSTRACT

A process for preparing biphenyl-4-carbonitrile of the formula

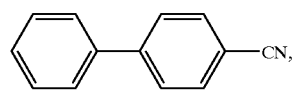

(I)

in which biphenyl is reacted with cyanogen chloride in the presence of anhydrous aluminum chloride.

6 Claims, No Drawings

METHOD FOR THE PRODUCTION OF BIPHENYL-4-CARBONITRILE

This is a 371 national stage application of International Patent Application No. PCT/EP02/12008, filed on Oct. 28, 2002, that has priority benefit of both European Patent Application No. 011258522, filed on Oct. 30, 2001.

The present invention relates to a process for preparing biphenyl-4-carbonitrile of the formula

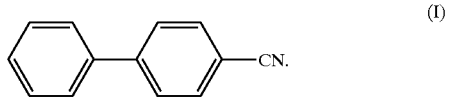

(I)

Biphenyl-4-carbonitrile is an important intermediate, for example in the synthesis of active pharmaceutical ingredients (see, for example, WO-A-01/22951).

Numerous processes for preparing biphenyl-4-carbo-nitrile are known. These can be classified into essentially three categories:
1. exchange of the halogen in 4-halobiphenyls for the cyano group
2. conversion of the function group in 4-substituted biphenyls to the cyano group
3. coupling of p-substituted benzonitriles with phenyl compounds.

These processes have the disadvantage that they require expensive starting materials and/or reagents which are unavailable in large amounts and some of which produce large amounts of heavy metal wastes. In addition, some of them do not afford pure products; for example, biphenyl-4-carbonitrile which is commercially available in small amounts (Aldrich) is contaminated by approx. 5% of the bromo compound.

It is an object of the present invention to provide a process for preparing biphenyl-4-carbonitrile, which only requires inexpensive starting materials which are available in large amounts and does not afford any problematic wastes.

According to the invention, this object is achieved by the process of claim 1.

It has been found that, surprisingly, biphenyl, which is available in large amounts, can be reacted with cyanogen chloride in the presence of anhydrous aluminum chloride, in good yield and without significant formation of isomeric or polycyanated by-products, directly to give the desired biphenyl-4-carbonitrile.

The anhydrous aluminum chloride and the cyanogen chloride are preferably used in an amount of in each case from 1.0 to 1.5 mol for 1 mol of biphenyl.

It is appropriate to carry out the process according to the invention in an inert solvent. This refers to any solvent which reacts significantly more slowly than biphenyl, if at all, under the reaction conditions. Preference is given to using halogenated aromatic solvents, for example chlorobenzene, bromobenzene or dichlorobenzenes. Particular preference is given to chlorobenzene.

The process according to the invention is advantageously carried out at reaction temperatures of from approx. 60 to 130° C.

The reaction may be carried out in various ways; for example, the biphenyl may be initially charged and then first the aluminum chloride and then the cyanogen chloride may be added. However, it is also possible to initially charge the aluminum chloride and then to introduce the cyanogen chloride and finally to add the biphenyl.

The workup may be effected in the customary manner for Friedel-Crafts reactions with aluminum chloride, for example by dissolving the aluminum salts in a lot of acid, thus bringing them into the aqueous phase, or precipitating them with a little water and filtering them off.

The examples which follow illustrate the performance of the process according to the invention, but should not be regarded as being restrictive.

EXAMPLE 1

50 g (0.324 mol) of biphenyl were dissolved at 25° C. under nitrogen in 200 ml of chlorobenzene. Subsequently, 51.88 g (0.389 mol) of anhydrous aluminum chloride were added and the mixture was stirred for 15 min. At 20–25° C., 23.92 g (0.389 mol) of cyanogen chloride were introduced thereto within one hour. On completion of addition, the mixture was stirred at 25° C. for another 30 min and subsequently heated to 110° C. After 4 h at this temperature, the reaction solution was diluted with 200 ml of chlorobenzene and cooled to 70–80° C. The reaction solution was then poured onto 600 ml of ice-cooled concentrated hydrochloric acid. The mixture was filtered and then the phases were separated. The aqueous phase was extracted once more with 100 ml of chlorobenzene. The combined organic phases were washed once with 300 ml of saturated sodium hydrogen carbonate solution, dried over sodium sulfate and filtered. The solvent was distilled off under reduced pressure and the solid obtained in this way was dried at 50° C./10 mbar for 24 h. 54.0 g (93%) of a yellow solid were obtained and, after treatment with 3.0 g of activated carbon, were recrystallized from isopropanol/water. Yield: 41.8 g (72%) of slightly yellowish crystals.

$^{13}$C NMR (CDCl$_3$): δ=145.69 (s); 139.20 (s); 132.59 (s); 129.12 (s); 128.67 (s); 127.74 (s); 127.23 (s); 118.91 (s); 110.98 (s).

EXAMPLE 2

50 g (0.324 mol) of biphenyl were dissolved at 25° C. under nitrogen in 200 ml of chlorobenzene. Subsequently, 51.88 g (0.389 mol) of anhydrous aluminum chloride were added and the mixture was stirred for 15 min. At 20–25° C., 23.92 g (0.389 mol) of cyanogen chloride were introduced thereto within one hour. On completion of addition, the reaction mixture was stirred at 25° C. for another 30 min and subsequently heated to 110° C. After 4 h at this temperature, the reaction solution was diluted with 200 ml of chlorobenzene and cooled to 70–80° C. 40 ml of water were then added dropwise within 30 min. Subsequently, the mixture was cooled to 20° C. and the precipitated aluminum salts were filtered off. The filter residue was washed twice more with 100 ml each time of chlorobenzene. The combined organic phases were concentrated by evaporation and the thus obtained residue was dried at 50° C./10 mbar. 52.8 g (91%) of a yellow solid were obtained and, according to GC, contained 90.5% biphenyl-4-carbonitrile.

EXAMPLE 3

51.88 g (0.389 mol) of aluminum chloride were suspended under nitrogen at 25° C. in 150 ml of chlorobenzene. Subsequently, 23.92 g (0.389 mol) of cyanogen chloride were introduced within 45 min. After a postreaction time of 15 min, the mixture was heated to 90° C. A solution of 50 g (0.324 mol) of biphenyl in 50 ml of chlorobenzene was then added dropwise to the suspension within one hour. Subsequently, the mixture was brought to 110° C. and allowed to react for 4 h. The reaction solution was then discharged onto 200 ml of water at 90° C. within one hour. The reaction vessel was flushed with 100 ml of chlorobenzene and the phases were left to separate. Once the aqueous phase had been discharged, the organic phase was washed at 90° C. with 200 ml of water. The thus obtained organic phase was subsequently stirred at 40° C. with 5 g of activated carbon for 30 min and then filtered. Subsequently, the organic phase was concentrated to dryness by evaporation. After drying at 50° C./10 mbar, 57.2 g (98.5%) of a yellow solid were obtained and, according to quantitative $^{13}$C NMR analysis, contained approx. 80% biphenyl-4-carbonitrile.

What is claimed is:

1. A process for preparing biphenyl-4-carbonitrile of the formula

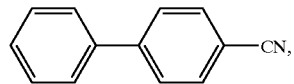

(I)

characterized in that biphenyl is reacted with cyanogen chloride in the presence of anhydrous aluminum chloride.

2. The process of claim 1, characterized in that the anhydrous aluminum chloride and the cyanogen chloride are each used in an amount of from 1.0 to 1.5 mol per 1 mol of biphenyl.

3. The process of claim 1, characterized in that the reaction is carried out in a halogenated aromatic solvent.

4. The process of claim 3, characterized in that the halogenated aromatic solvent used is chlorobenzene.

5. The process of claim 2, characterized in that the reaction is carried out in a halogenated aromatic solvent.

6. The process of claim 5, characterized in that the halogenated aromatic solvent used is chlorobenzene.

* * * * *